(12) United States Patent
Schieke

(10) Patent No.: US 11,213,220 B2
(45) Date of Patent: Jan. 4, 2022

(54) METHOD FOR DETERMINING IN VIVO TISSUE BIOMARKER CHARACTERISTICS USING MULTIPARAMETER MRI MATRIX CREATION AND BIG DATA ANALYTICS

(71) Applicant: CUBISME, INC., Milwaukee, WI (US)

(72) Inventor: Moira F. Schieke, Milwaukee, WI (US)

(73) Assignee: CUBISME, INC., Milwaukee, WI (US)

( * ) Notice: Subject to any disclaimer, the term of this patent is extended or adjusted under 35 U.S.C. 154(b) by 816 days.

(21) Appl. No.: 14/821,700

(22) Filed: Aug. 8, 2015

(65) Prior Publication Data
US 2016/0038095 A1 Feb. 11, 2016

Related U.S. Application Data

(60) Provisional application No. 62/035,873, filed on Aug. 11, 2014, provisional application No. 62/041,787, filed on Aug. 26, 2014.

(51) Int. Cl.
*A61B 5/055* (2006.01)
*G16H 50/70* (2018.01)
(Continued)

(52) U.S. Cl.
CPC ............ *A61B 5/055* (2013.01); *A61B 5/7485* (2013.01); *G01R 33/56* (2013.01);
(Continued)

(58) Field of Classification Search
None
See application file for complete search history.

(56) References Cited

U.S. PATENT DOCUMENTS 6,567,684 B1 * 5/2003 Chenevert ............ A61B 5/055
324/309
6,956,373 B1 10/2005 Brown et al.
(Continued)

FOREIGN PATENT DOCUMENTS

EP 3 043 318 7/2016
EP 3 117 771 A2 1/2017
(Continued)

OTHER PUBLICATIONS

Antipolis, Sophia, "Median Technologies strengthens IP portfolio with US patent," MEDIAN Technologies (ALMDT), Sep. 10, 2015.
(Continued)

*Primary Examiner* — James M Kish
(74) *Attorney, Agent, or Firm* — Foley & Lardner LLP

(57) ABSTRACT

A method for determining MRI biomarkers for in vivo issue includes the steps of obtaining raw data concerning the in vivo tissue from a MRI machine; processing the raw data to obtain parameter maps; when applicable, registering images such that the exact same tissue at serial points can be analyzed; applying a grid over a region of interest to create sub-regions of interest (SROIs); inserting parameter measures for each SROI into a spreadsheet program to create a large 3D data matrix; applying standard big-data analytics including data mining and statistics of matrix measures to find patterns of measurement values or measure changes (which may include established biomarkers). A medical imaging software program is used to obtain the parameter maps from the raw data and place multiple grids over the SROIs. 3D matrix measures may be data mined and analyzed using standard big-data analytics.

14 Claims, 6 Drawing Sheets

(51) Int. Cl.
*A61B 5/00* (2006.01)
*G16H 10/20* (2018.01)
*G16H 30/40* (2018.01)
*G16H 20/40* (2018.01)
*G01R 33/56* (2006.01)
*G01R 33/563* (2006.01)
*G06T 7/00* (2017.01)

(52) U.S. Cl.
CPC ......... *G01R 33/5602* (2013.01); *G16H 10/20* (2018.01); *G16H 20/40* (2018.01); *G16H 30/40* (2018.01); *G16H 50/70* (2018.01); *A61B 5/4842* (2013.01); *A61B 5/4848* (2013.01); *A61B 2576/00* (2013.01); *G01R 33/5608* (2013.01); *G01R 33/5635* (2013.01); *G06T 7/0016* (2013.01)

(56) References Cited

U.S. PATENT DOCUMENTS

| | | | |
|---|---|---|---|
| 8,509,570 | B2 | 8/2013 | Degani et al. |
| 8,605,980 | B2 | 12/2013 | Li et al. |
| 8,768,431 | B2 | 7/2014 | Ross et al. |
| 8,781,214 | B2 | 7/2014 | Davis et al. |
| 8,805,619 | B2 | 8/2014 | Sorensen et al. |
| 8,818,484 | B2* | 8/2014 | Liew ............... A61B 6/482 600/407 |
| 8,873,836 | B1 | 10/2014 | Dietrich et al. |
| 9,092,691 | B1 | 7/2015 | Beaumont et al. |
| 9,165,362 | B2 | 10/2015 | Siewerdsen et al. |
| 9,424,639 | B2 | 8/2016 | Jacob |
| 9,615,028 | B2 | 4/2017 | Mizutani et al. |
| 10,452,813 | B2 | 10/2019 | Sorenson et al. |
| 10,762,627 | B2 | 9/2020 | Strommer et al. |
| 2002/0186818 | A1* | 12/2002 | Arnaud ............ A61B 6/583 378/165 |
| 2002/0193677 | A1 | 12/2002 | Thornton |
| 2003/0072479 | A1 | 4/2003 | Totterman et al. |
| 2006/0262970 | A1 | 11/2006 | Boese et al. |
| 2006/0269476 | A1 | 11/2006 | Kuo |
| 2008/0097186 | A1* | 4/2008 | Biglieri ............ A61B 5/055 600/407 |
| 2009/0161928 | A1 | 6/2009 | Khamene et al. |
| 2009/0208075 | A1* | 8/2009 | Fischer ............ G06T 7/11 382/128 |
| 2010/0142786 | A1* | 6/2010 | Degani ............ A61B 5/055 382/131 |
| 2010/0158332 | A1 | 6/2010 | Rico et al. |
| 2010/0284927 | A1* | 11/2010 | Lu ............ A61K 49/085 424/9.2 |
| 2011/0243417 | A1 | 10/2011 | Madabhushi et al. |
| 2011/0312520 | A1 | 12/2011 | Kennedy et al. |
| 2013/0004044 | A1 | 1/2013 | Ross et al. |
| 2013/0197349 | A1* | 8/2013 | Blumhagen ...... G01R 33/481 600/411 |
| 2013/0329973 | A1 | 12/2013 | Cao et al. |
| 2014/0003697 | A1 | 1/2014 | Qian et al. |
| 2014/0010429 | A1 | 1/2014 | Highnam et al. |
| 2014/0010430 | A1 | 1/2014 | Chandelier et al. |
| 2014/0037172 | A1 | 2/2014 | Madabhushi et al. |
| 2014/0064580 | A1 | 3/2014 | Madabhushi et al. |
| 2014/0079302 | A1 | 3/2014 | Sato et al. |
| 2014/0086836 | A1 | 3/2014 | Burnham et al. |
| 2014/0101080 | A1 | 4/2014 | Lee et al. |
| 2014/0126794 | A1 | 5/2014 | Ahn et al. |
| 2014/0153795 | A1 | 6/2014 | Lenox |
| 2014/0185888 | A1 | 7/2014 | Kelm et al. |
| 2014/0185900 | A1 | 7/2014 | Lee et al. |
| 2014/0195472 | A1 | 7/2014 | Kawagishi |
| 2014/0205163 | A1 | 7/2014 | Stark et al. |
| 2014/0219535 | A1 | 8/2014 | Chen et al. |
| 2014/0228667 | A1 | 8/2014 | Dankerl et al. |
| 2014/0233826 | A1 | 8/2014 | Agaian et al. |
| 2014/0241606 | A1 | 8/2014 | Park et al. |
| 2014/0309511 | A1 | 10/2014 | Stal |
| 2015/0003706 | A1 | 1/2015 | Eftestol et al. |
| 2015/0093007 | A1 | 4/2015 | Beaumont et al. |
| 2015/0198688 | A1 | 7/2015 | Cetingul |
| 2015/0352363 | A1 | 12/2015 | Mcintyre et al. |
| 2016/0019693 | A1 | 1/2016 | Silbersweig et al. |
| 2016/0038095 | A1 | 2/2016 | Schieke |
| 2016/0086326 | A1 | 3/2016 | Raschke et al. |
| 2016/0117816 | A1 | 4/2016 | Taylor |
| 2016/0203263 | A1 | 7/2016 | Maier et al. |
| 2016/0217576 | A1 | 7/2016 | Kabus et al. |
| 2016/0292194 | A1 | 10/2016 | Farkash |
| 2016/0350933 | A1 | 12/2016 | Schieke |
| 2016/0350946 | A1 | 12/2016 | Schieke et al. |
| 2017/0046839 | A1 | 2/2017 | Paik et al. |
| 2017/0261584 | A1 | 9/2017 | James et al. |
| 2017/0263023 | A1 | 9/2017 | Zhou |
| 2017/0358079 | A1 | 12/2017 | Gillies et al. |
| 2018/0114312 | A1 | 4/2018 | Palma |
| 2018/0165867 | A1 | 6/2018 | Kuhn et al. |
| 2020/0281539 | A1 | 9/2020 | Hoernig et al. |

FOREIGN PATENT DOCUMENTS

| | | |
|---|---|---|
| WO | WO-2015/175746 A1 | 11/2015 |
| WO | WO-2016/206942 A1 | 12/2016 |
| WO | WO-2017/151757 | 9/2017 |

OTHER PUBLICATIONS

Ashraf,B. Ahmed et al., "Identification of Intrinsic Imaging Phenotypes for Breast Cancer Tumors: Preliminary Associations with Gene Expression Profiles," Radiology: vol. 272:No. 2, 2014.

Baselga, et al., "Everolimus in Postmenopausal Hormone-Receptor 2013 Positive Advanced Breast Cancer," New England Journal of Medicine, 2012, 366, pp. 520-529.

Boes, et at., "Image Registration for Quantitative Parametric Response Mapping of Cancer Treatment Response," Feb. 2014, Translational Oncology, vol. 7, No. 1, pp. 101-110.

Bornn, Luke et al., "Herded Gibbs Sampling," Mar. 16, 2013, arXiv:1301.4168v2 [cs.LG].

Buckley, David,"Uncertainty in the Analysis of Tracer Kinetics Using Dynamic Contrast-Enhanced T1-Weighted MRI," Magnetic Resonance in Medicine, Feb. 20, 2002,47, pp. 601-606.

Chan, et al., "Detection of Prostate Cancer by Integration of Line-Scan Diffusion, T2-Mapping and T2-Weighted Magnetic Resonance Imagine; a Multichannel Statistical Classifier," Medical Physics, Sep. 2003, vol. 30, No. 9, 2390-2398.

Colen, et al., "NCI Workshop Report: Clinical and Computational Requirements for Correlating Imaging Phenotypes with Genomics Signatures," Translational Oncology, Oct. 2014, vol. 7, No. 5, pp. 565-569.

Determining Single Voxel Value from Larger Region of Interest (ROI), Dec. 18, 2014.

Ellingson, et al,"Graded Functional Diffusion Map 2013 Defined Characteristics of Apparent Diffusion Coefficients Predict Overall Survival in Recurrent Glioblastoma Treated with Bevacizumab," Neuro-Oncology, 2011, 13, pp. 1151-1161.

Ellingson, et al., "Volumetric Analysis of Functional Diffusion Maps is a Predictive Imaging Biomarker for Cytotoxic and Anti-Angiogenic Treatments in Malignant Gliomas," Journal of Neuro-Oncology, 2011, 102, 95-103.

Galavis, et al.,"Variability of Textural Features in FDG PET Images Due to Different Acquisition Modes and Reconstruction Parameters," Acta Oncologica, 2010, 49, pp. 1012-1016.

Galban J. Craig, "The Parametric Response Map: An Imaging Biomarker for Early Cancer Treatment Outcome," National Institute of Health, 2009, 15(5): 572-576. doi:10.1038/nm.1919.

Galbraith, et al., Reproducibility of Dynamic Contrast-Enhanced MRI in Human Muscle and Tumours: Comparison of Quantitative and Semi-Quantitative Analysis, NMR in Biomedicine, Feb. 20, 2002, 15, pp. 132-142.

Gillies, et al., "MRI of the Tumor Microenvironment," Journal of Magnetic Resonance Imaging, 2002, 16, pp. 430-450.

(56) References Cited

OTHER PUBLICATIONS

Haq, et al, "A Data-Driven Approach to Prostate Cancer Detection From Dynamic Contrast Enhanced MRI," PubMed Central Canada, 2017 pp. 1-27.

Haq, et al., "A Data-Driven Approach to Prostate Cancer Detection From Dynamic Contrast Enhanced MRI," Computerized Medical Imaging and Graphics, 2014, pp. 1-9.

Heidbreder, G.R.; Maximum Entropy and Bayesian Methods; Kluwer Academic Publishers; ISBN 0-7923-2851-5; 1993.

International Search Report and Written Opinion for PCT/US2017/040456 dated Oct. 19, 2017 (14 pages).

Irani, M. et al.; Motion Analysis for Image Enhancement: Resolution, Occlusion, and Transparency; Journal of Visual Communication and Image Representation; vol. 4; No. 4; Dec. 1993; pp. 325-335.

Irani, Michal et al., "Motion Analysis for Image Enhancement: Resolution Occlusion, and Transparency," Journal of Visual Communication and Image Representation, Institute of Computer Science, The Hebrew University of Jerusalem, Aug. 23, 1993, vol. 4, No. 4, December, pp. 324-335.

Kamal, Nasrollahi et al., "Super-Resolution: A Comprehensive Survey," Machine Vision & Applications, 2014, 25(6), 1423-1468. 10.1007/s00138-014 0623-4.

Kwak, et al., "Automated Prostate Cancer Detection Using T2-Weighted and High-B-Value Diffusion-Weighted Magnetic Resonance Imaging," Medical Physics, May 2015, vol. 42, No. 5, pp. 2368-2378.

Kwak, et al., "Correlation of Magnetic Resonance Imaging With Digital Histopathology in Prostate," Int J CARS, 2016, 11, pp. 657-666.

Langer, et al., "Prostate Cancer Detection With Multi-parametric MRI: Logistic Regression Analysis of Quantitative T2, Diffusion-Weighted Imaging, and Dynamic Contrast-Enhanced MRI," Journal of Magnetic Resonance Imaging, 2009, 30, pp. 327-334.

Li, et al., "Cell Membrane Water Exchange Effects in Prostate DCE-MRI," Journal of Magnetic Resonance, vol. 218, 2012, pp. 77-85.

Maani, et al., "Voxel-Based Texture Analysis of the Brain," Plos One, Mar. 10, 2015, pp. 1-19.

Maenpaa, et al., "Texture Analysis With Local Binary Patterns," WSPC, May 13, 2004, 8:19, pp. 1-20.

Method for Determining In Vivo Tissue Biomarker Characteristics Using Multiparameter MRI Matrix Creation and Big Data Analytics Draft application.

Moffat, et al., "Functional Diffusion Map: A Noninvasive MRI Biomarker for Early Stratification of Clinical Brain Tumor Response," Proceedings of the National Academy of Sciences, 2005, 102, pp. 5524-5529.

Moradi, et al., "Multiparametric MRI Maps for Detection and Grading of Dominant Prostate Tumors," Journal of Magnetic Resonance Imaging, 2012, 35, pp. 1403-1413.

Nasrollahi, K. et al.; Super-resolution: A comprehensive survey. Machine Vision & Applications, 25(6), 1423-1468, 2014. 10.1007/s00138-014-0623-4.

Niaf, et al., "Computer-Aided Diagnosis of Prostate Cancer in the Peripheral Zone Using Multiparametric MRI," Phys. Med. Biol. 2012, 57, pp. 3833-3851.

Oto, et. al, "Diffusion-Weighted and Dynamic Contrast-Enhanced MRI of Prostate Cancer: Correlation of Quantitative MR Parameters With Gleason Score and Tumor Angiogenesis," American Journal of Roentgenology, 2011, 197, pp. 1382-1390.

Padhani, et al., "Reproducibility of Quantitative Dynamic MRI of Normal Human Tissues," NMR in Biomedicine,2002, 15, pp. 143-153.

Peng, et al., "Quantitative Analysis of Multiparametric Prostate MR Images: Differentiation Between Prostate Cancer and Normal Tissue and Correlation with Gleason Score—A Computer-aided Diagnosis Developmental Study," Radiology, Jun. 2013, vol. 267: No. 3, pp. 787-796.

Purysko, et al., "LI-RADS: A Case-based Review of the New Categorization of Liver Findings in Patients With End-Stage Liver Disease," RadioGraphics, Nov.-Dec. 2012, vol. 32, No. 7, pp. 1977-2012.

Rijpkema, et al., "Method for Quantitative Mapping of Dynamic MRI Contrast Agent Uptake in Human Tumors," Journal of Magnetic Resonance Imaging, 2001, 14, pp. 457-463.

Roberts, et al., "The Effect of Blood Inflow and B1-Field Inhomogeneity on Measurement of the Arterial Input Function in Axial3D Spoiled Gradient Echo Dynamic Contrast-Enhanced MRI," Magnetic Resonance in Medicine, 2010, 65, 108-119.

Senseney, et al., "Tumor Treatment Response Identification Using Combination Post-Treatment Mapping to Quantify Voxel-Wise Multiparameter MRI Biomarker Changes: A Simulation Study," Dana-Farber Cancer Institute.

Senseney, et al., "Tumor Treatment Response Identification Using Combination Post-Treatment Mapping to Quantify Voxel-Wise Multiparameter MRI Biomarker Changes: A Simulation Study. International Symposium on Biomedical Imaging," Barcelona, Spain, May 2012.

Senseney, Justin et al., "Tumor Treatment Response Identification Using Combination Post-Treatment Mapping to Quantify Voxel-Wise Multiparameter MRI Biomarker Changes: A Simulation Study," Imaging Sciences Lab, Center for Information Technology, National Institute of Health, Besthesda, MD.

Shah et al., "Decision Support System for Localizing Prostate Cancer based on Multiparametric Magnetic Resonance Imaging," Medical Physics, Jul. 2012, vol. 39, No. 7, 11 pages.

Tae Kwak, Jin, "Prostate Cancer: A Correlative Study of Multiparametric MR Imaging and Digital Histopathology," Radiology, Orginal Research Genitourinary Imaging, vol. 000: No. 0, 2017.

U.S. Non-Final Office Action on U.S. Appl. No. 14/821,703 dated Mar. 22, 2017 (57 pages).

U.S. Office Action on U.S. Appl. No. 15/165,644 dated Nov. 30, 2017.

Wang, et al., "Computer Aided-Diagnosis of Prostate Cancer on Multiparametric MRI: A Technical Review of Current Research," BioMed Research International, Aug. 2014, pp. 1-11.

Wang, Shijun et al., "Computer Aided-Diagnosis of Prostate Cancer on Multiparametric MRI: A Technical Review of Current Research," Hindawi Publishing Corporation, Aug. 28, 2014, 12 pages.

Yang, et al., "Comparison of Quantitative Parameters in Cervix Cancer Measured by Dynamic Contrast 2013 Enhanced MRI and CT," Magnetic Resonance in Medicine, 2010, 63, pp. 1601-1609.

Yang, et al., "Reproducibility Assessment of a Multiple Reference Tissue Method for Quantitative Dynamic Contrast Enhanced 2013 MRI Analysis," Magnetic Resonance in Medicine, 2009, 61, pp. 851-859.

Non-Final Office Action on U.S. Appl. No. 15/640,107 dated Jan. 23, 2019.

International Search Report and Written Opinion in PCT/US2018/028679 dated Jan. 29, 2019 (14 pages).

Extended European Search Report in EP 17821418.5 dated Jul. 17, 2020 (10 pages).

Notice of Allowance on U.S. Appl. No. 15/640,107 dated Mar. 10, 2020.

3D Human Models from 1D, 2D & 3D Inputs @3DBODY.TECH Oct. 17, 2018. Retrieved from the Internet on Feb. 17, 2021 URL: https://www.slideshare.net/AlfredoBallesterFern/3-dbt2018-id36ballesterv04pdf.

CORADS-AI—Grand Challenge. Retrieved from the Internet on Feb. 17, 2021 URL: https://github.com/microsoft/InnerEye-DeepLearning.

Extended European Search Report in EP 18788304.6 dated Jan. 13, 2021 (9 pages).

GitHub—Microsoft InnerEye DeepLearning Medical Imaging Deep Learning library to train and deploy models on Azure Machine Learning and Azure Stack. Retrieved from the Internet on Feb. 17, 2021 URL: https://grand-challenge.org/algorithms/corads-ai/.

Lessmann et al., Automated Assessment of COVID-19 Reporting and Data System and Chest CT Severity Scores in Patients Sus-

(56) References Cited

OTHER PUBLICATIONS pected of Having COVID-19 Using Artificial Intelligence. Radiology: vol. 298: No. 1—Jan. 2021, https://pubs.rsna.org/doi/10.1148/radiol.2020202439.
MedSeg—free medical segmentation online. Retrieved from the internet on Feb. 17, 2021 URL: https://www.medseg.ai.
Non-Final Office Action on U.S. Appl. No. 15/959,142 dated Mar. 22, 2021.
Photo Tourism: Exploring Photo Collections in 3D. Retrieved from the Internet on Feb. 17, 2021 URL: http://phototour.cs.washington.edu/Photo_Tourism.pdf.
Point set registration—Wikipedia. Retrieved from the Internet on Feb. 17, 2021 URL: https://en.wikipedia.org/wiki/Point_set_registration.
Project InnerEye—Democratizing Medical Imaging AI—Microsoft Research. Retrieved from the Internet on Feb. 17, 2021 URL: https://www.microsoft.com/en-us/research/project/medical-image-analysis/.

* cited by examiner

| MRI Technique | Parameter | Description |
|---|---|---|
| Standard | T1-mapping | quantitative T1 measures |
|  | T2-mapping | quantitative T2 measures |
| DCE-MRI | Ktrans | indicator of degree of vessel leakage and tumor angiogenesis |
|  | Ve | volume of exchange of contrast |
|  | ΔKtrans | difference in Ktrans values between standard modeling and that considering transcytolemmal water exchange (Springer) |
|  | intracellular tau | mean intracellular water lifetime (Springer) |
| DWI | ADC | indicator of water restriction |
|  | various DWI parameters | |
| ISI | R* | related to tissue oxygenation |

Fig. 6

METHOD FOR DETERMINING IN VIVO TISSUE BIOMARKER CHARACTERISTICS USING MULTIPARAMETER MRI MATRIX CREATION AND BIG DATA ANALYTICS

RELATED APPLICATION

This application claims priority to U.S. provisional application No. 62/035,873, filed on Aug. 11, 2014, and to U.S. provisional application No. 62/041,787, filed on Aug. 26, 2014, all of which are incorporated herein by reference in their entirety.

BACKGROUND OF THE DISCLOSURE

Field of the Disclosure

The present invention relates generally to determination of tissue biomarkers and more specifically to a method for determining the effectiveness of a treatment for in vivo diseased tissue, which allows a treatment to be more quickly and precisely evaluated than that of the prior art. This method can be used for precise identification of tumor tissue biomarkers, as well as early changes following cancer treatments for early selection of optimal therapy.

Brief Description of the Related Art

Clinical cancer imaging advancements are greatly needed for optimal management of cancer patients in a new age of targeted therapies. Current CT methods are not sufficiently sensitive or specific to early changes in disease, especially for newer targeted agents. As imaging markers lag, advancements are being made in developing novel targeted drugs, describing tissue-based tumor genetics, and developing sensitive blood tumor markers. Microarray technology has allowed for this rapid pace of advancement by turning the attention of scientists to more powerful "big data." In the arena of MRI research, continual development of increasingly complex and detailed information on the tumor microenvironment from indices of the tumor rate of angiogenesis to water-sodium balance provides a new opportunity.

Ongoing research proves the genetic diversity of tumors and metastatic clones, and beckons an era of cancer imaging sensitive to this diversity. The success of targeted treatments for cancer has been dampened by the tremendous plasticity of tumors to engage escape pathways and to elude these powerful therapies. Many clinical trials have shown early success of the targeted treatment with improved progression-free survival, only to be followed by aggressive tumor regrowth and no net improvement in overall survival. Successful use of targeted therapies for treatment of cancer will require methods for best selection of combination "cocktail" targeted therapies to match tumor genetics, as well as early identification of treatment failure to allow for early modifications in therapy.

Current standard clinical techniques for determining tumor response or progression are inadequate for this task. For the most part, the current standard CT criteria for measuring tumor size, Response Evaluation Criteria in Solid Tumors (RECIST), is limited to assessment of morphological changes in tumors that can takes months following chemotherapy. In addition, newer targeted therapies most often do not affect tumor size. Although PET has proven applications for monitoring tumor responses and can be used with targeted therapies, many tumors are not PET-avid, this modality suffers from poor image resolution and large partial volume errors, and it provides only unidimensional physiological data after administration of a select radiopharmaceutical. In addition, PET has relatively large measurement errors associated with variability in background normal tissue tracer uptake, making it less sensitive to small changes and small volume changes. PET Response in Solid Tumors (PERCIST) is the PET analog of RECIST, and requires extensive controls such as tracer dosage and timing of imaging to identify population-based tumor responses. In comparison, multiparameter MRI can provide many different forms of tumor data in a single study, innumerable studies demonstrate the ability of MRI to detect changes after targeted therapies, and MRI has superior tumor tissue contrast and resolution.

In the MRI cancer imaging research arena, rapid advancements are being made in characterizing the tumor microenvironment, from indices of tumor angiogenesis to sodium-water balance. The power of MRI lies in its ability to "interrogate" tissues to provide information on anatomic morphology with superior soft tissue contrast, as well as provide an unlimited number of quantitative measures or "parameters" of tissue properties and physiology. Given the enormity of the data, the challenge for the successful clinical application of multiparameter MRI is creating manageable and reproducible tools. Specifically, techniques are needed that overcome basic sources of error that hinder the wider applicability of MRI techniques, such as partial volume errors. Standard methods for quantifying tumor or tissue changes most often involve tumor segmentation to obtain a defined region or volume of interest (FIG. 1) over the entire tissue of interest. If Dynamic Contrast-Enhanced MRI (DCE-MRI), is used as an example, not only do innumerable published studies address sources of error and poor measure reproducibility, but clinical studies demonstrate a lack of sensitivity to expected tumor changes after treatment.

An article in the journal, Radiology, shows success in using array types statistics for analysis of a large number of tumor quantitative measures for breast cancer. These authors, however, use a limited and standard single "region of interest" over the entire tissue of interest, which is a commonly used standard technique prone to large measurement errors.

Sophisticated voxel-wise mapping techniques, such as diffusion weighted imaging (DWI) "functional diffusion maps" (FDM) patented by the University of Michigan, create maps of voxel-wise changes by overlaying pre- and post-treatment parameter maps. Multiple studies have successfully proven that FDM provide an imaging biomarker of tumor response in glioma patients. Improved results are likely related to reduced partial volume errors, with identification of changes only in voxels with high percent tumor tissue and relative exclusion of voxels with higher partial voluming measurement error. These technically challenging methods, however, are prone to errors caused by low signal-to-noise at the level of a voxel, which limits its use to MRI techniques with high tumor contrast-to-noise ratio such as DWI. In addition, these techniques require quantification of tumor volumes and assumptions on tumor extent, and are thus prone to some of the errors associated with standard tumor "region of interest" techniques. These methods utilize a single MRI parameter, such as DWI, and cannot or have not been used with larger multiparameter datasets.

SUMMARY OF THE DISCLOSURE

The present invention provides a method for earlier and more precise identification of tissue biomarkers than that of the prior art. The method for identification of earlier and more precise tissue characteristics or changes, i.e., tissue sampling method, includes the following steps: obtaining raw data concerning in vivo tissue in at least one session or during at least one time point, for example before and after treatment, wherein the raw data may be obtained from, e.g., a MRI device or machine; processing the raw data with a software package to obtain different parameter maps; when applicable, registering images (e.g., the parameter maps) such that the exact same tissue (e.g., the in vivo tissue) at serial points can be analyzed; applying a grid over a region of interest using the software package to create multiple sub-regions of interest (SROIs) of the in vivo tissue so that the grid contains the SROIs of the in vivo tissue; obtaining first measures of different parameters for each of the SROIs of the in vivo tissue from all of the parameter maps; inserting the first measures of the different parameters obtained from each of the SROIs of the in vivo tissue into a spreadsheet program (or other matrix data collection software) operating on a computing device; mining the first measures of the different parameters for each of the SROIs from all of the parameter maps utilizing standard big-data analytics of parameter matrix datasets to find patterns of tissue properties (or characteristics) and/or changes (which may include identified tissue biomarkers). In an embodiment, the tissue sampling method may further include determining the identified tissue biomarkers through large scale clinical trials and comparing individual biomarkers to those found during the large scale clinical trials. In an embodiment, the tissue sampling method may further include using multiple changes of the identified tissue biomarkers in the SROIs for clinical management. In an embodiment, the tissue sampling method may further include providing a search kernel to identify tissue biomarker patterns within a MRI multi-parameter dataset for application for an individual patient. In an embodiment, the tissue sampling method may further include displaying the patterns of tissue properties (or characteristics) and/or changes on a display device, such as a computer monitor. In an embodiment, the tissue sampling method may further include mining multiple second measures of the different parameters for each of the SROIs with a data mining software program operating on the computing device.

It would be necessary to identify SROI tissue biomarkers by comparison with outcomes and/or biopsy results for a large number of patients to provide the reference or identification for SROI tissue biomarkers for individual patients. Large scale clinical trials are needed in order to prove the validity of each biomarker for subsequent individual patient management, such as for selecting individual cancer patient treatments. Large clinical trials may be utilized for various diseases (but specifically cancer) to determine various characteristics of patient tissue. Specific examples may include but not be limited to 1) precise and sensitive identification of diseased tissue, 2) precise biomarkers of tumor aggressiveness, 3) biomarkers of tumor tissue genetic characteristics (termed "radiogenomics"), 4) biomarkers of tumor tissue or other tissue early response to therapy, and 5) biomarkers of tumor tissue or other tissue early signs of failure to therapy. This method may be applied across the entire patient body, from head-to-toe. Specifically, tissue may be sampled across the various metastatic clones in a single patient with disseminated cancer from whole-body MRI datasets.

A magnetic resonance imaging (MRI) device or machine (or any other combined modality MRI machine, such as a positron emission tomography-magnetic resonance imaging (PET-MRI) machine) is used to obtain the raw data concerning the in vivo tissue. A freeware medical imaging or other standard commercial software program, i.e., the software package, may be used to obtain the different parameter maps from the raw data such as raw MRI data. The MRI device or machine may be used to place a plurality of grids containing a plurality of sub-regions of interest (SROIs) over the tissue of interest, i.e., the region of interest. SROI size may be optimized for specific image noise and registration characteristics, but could theoretically approximate the size of a single image voxel or pixel. Multiple parameters output values for each SROI are entered into a spreadsheet, such as Excel or other matrix data collection software. The spreadsheet entries are data mined by a software program, such as Excel Professional Plus or other data mining software, to find patterns of measures or measure changes across various parameters at single or serial time-points. The patterns of changes in the SROIs are compared to true patient clinical outcomes and biopsy results to determine tissue biomarkers. The plurality of SROI allow a tissue property or change to be evaluated more precisely given the smaller size of the SROI compared to standard ROI and with higher specificity given the large number of parameter characteristics evaluated. In addition, the size of the SROI larger than a single voxel, and incorporating ideally multiple voxels, improves the signal-to-noise ratio (SNR) which provides de-noised parameter measures. Increased precision of SROI measures, in turn, allows for earlier and more precise identification of SROI tissue biomarkers.

Accordingly, it is an object of the present invention to provide a tissue sampling method which utilizes multiparameter MRI datasets and data mining analytics to focus on identifying SROI of in vivo tissue that provide tissue biomarker information for clinical use in the management of patients, and specifically cancer patients.

It is another object of the present invention to provide a tissue sampling method, which circumvents the errors associated with standard "region of interest" segmentation and mapping techniques by ignoring most of in vivo tissue and only searching for SROI that "rule-in" biomarker changes.

It is another object of the present invention to provide a tissue sampling method, which uses a dense sampling strategy to create large three-dimensional (3D) multi-parameter MRI data matrices at a single or multiple time-points amenable to data mining and standard applied array statistics, such as those utilized for microarray statistics.

It is another object of the present invention to propose tightly packed subregion matrix creation used for large data samples and more precise tissue characterization.

It is another object of the present invention to provide a method, which includes the following steps: creating large matrix datasets collected from a large multitude of small region tissue sampling from a multitude of MRI parameter maps, and applying big-data analytics comprising the gamut of data mining and big-data statistical techniques to identify precise tissue biomarkers within subregions of diseased tissue, such as within malignant tumors.

It is another object of the present invention to provide a method for determining in vivo tissue precise biomarkers, which utilizes multiparameter MRI datasets and focuses on identifying subregions of in vivo tissue to provide more precise tissue quantitative data, circumvents the measurement errors associated with standard segmentation and mapping techniques, and provides more powerful and precise clinical tools for managing patient treatments. The method uses a dense sampling strategy to create large three-dimensional multiparameter MRI data arrays amenable to data mining analytics and statistics, which allows a tissue biomarker to be more quickly and precisely evaluated than that of the prior art.

It is another object of the present invention to provide a tissue sampling method, which allows a treatment to be more quickly and precisely evaluated than that of the prior art.

These, as well as other objects, steps, features, benefits, and advantages of the present disclosure, will now become clear from a review of the following detailed description of illustrative embodiments, the accompanying drawings, and the claims.

BRIEF DESCRIPTION OF THE DRAWINGS

The drawings disclose illustrative embodiments of the present disclosure. They do not set forth all embodiments. Other embodiments may be used in addition or instead. Details that may be apparent or unnecessary may be omitted to save space or for more effective illustration. Conversely, some embodiments may be practiced without all of the details that are disclosed. When the same reference number or reference indicator appears in different drawings, it may refer to the same or like components or steps.

Aspects of the disclosure may be more fully understood from the following description when read together with the accompanying drawings, which are to be regarded as illustrative in nature, and not as limiting. The drawings are not necessarily to scale, emphasis instead being placed on the principles of the disclosure. In the drawings:

FIG. 6 shows examples of parameter measures that could be applied for tumor array datasets.

Figure 1:
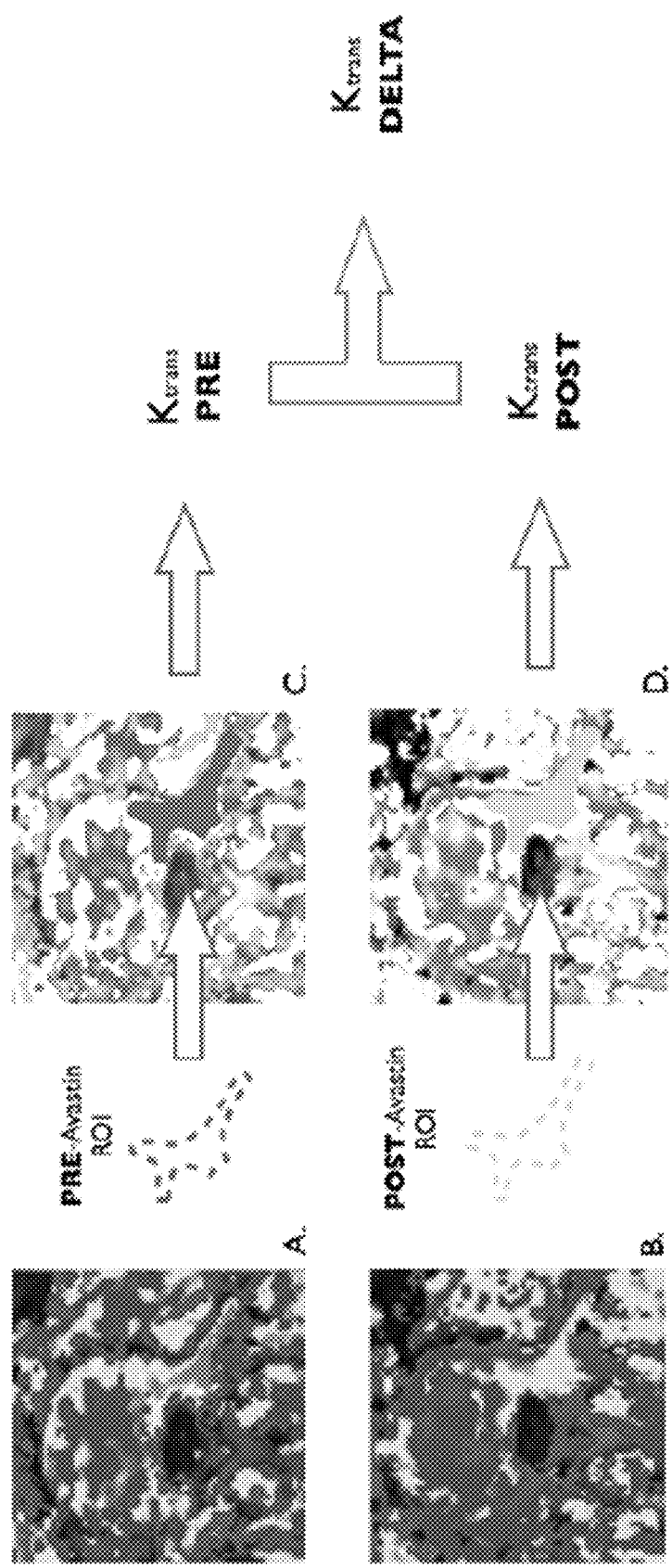
FIG. 1 is a schematic diagram of preliminary data and standard techniques.

While certain embodiments are depicted in the drawings, one skilled in the art will appreciate that the embodiments depicted are illustrative and that variations of those shown, as well as other embodiments described herein, may be envisioned and practiced within the scope of the present disclosure.

DETAILED DESCRIPTION OF THE INVENTION

Illustrative embodiments are now described. Other embodiments may be used in addition or instead. Details that may be apparent or unnecessary may be omitted to save space or for a more effective presentation. Conversely, some embodiments may be practiced without all of the details that are disclosed.

Multiparameter MRI provides the greatest opportunity for specific identification of diverse and small changes in small tumor volumes. The success, knowledge, and experience from microarray technology and data mining can be applied to multiparameter MRI "big data." In the field of cancer research, such an approach is needed in order for imaging science to create a three-dimensional (3D) corollary to the rapidly advancing field of tissue-based microarrays. For patients with metastatic disease, this 3D corollary may be a powerful clinical tool for early and specific biomarker identification across the spectrum of metastatic clones, providing the best opportunity to tailor and adapt therapy to improve patient survival.

Figure 2:
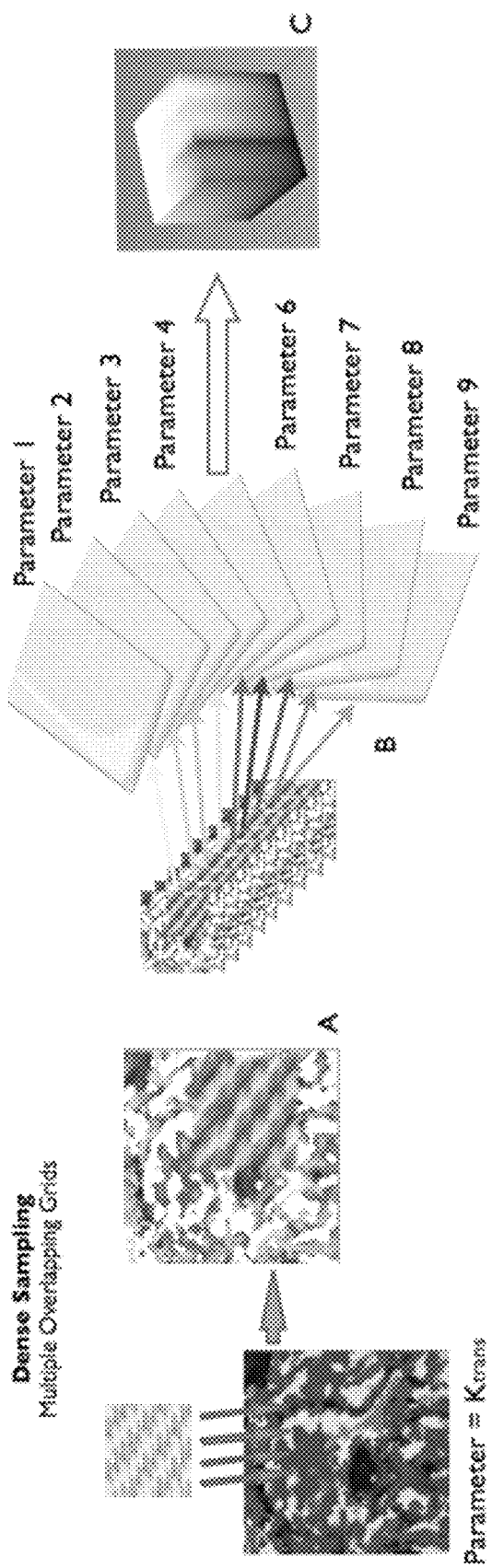
FIG. 2 is a schematic diagram of dense sampling and creation of a three-dimensional (3D) multi-parameter magnetic resonance imaging (MRI) data array.
Figure 3:
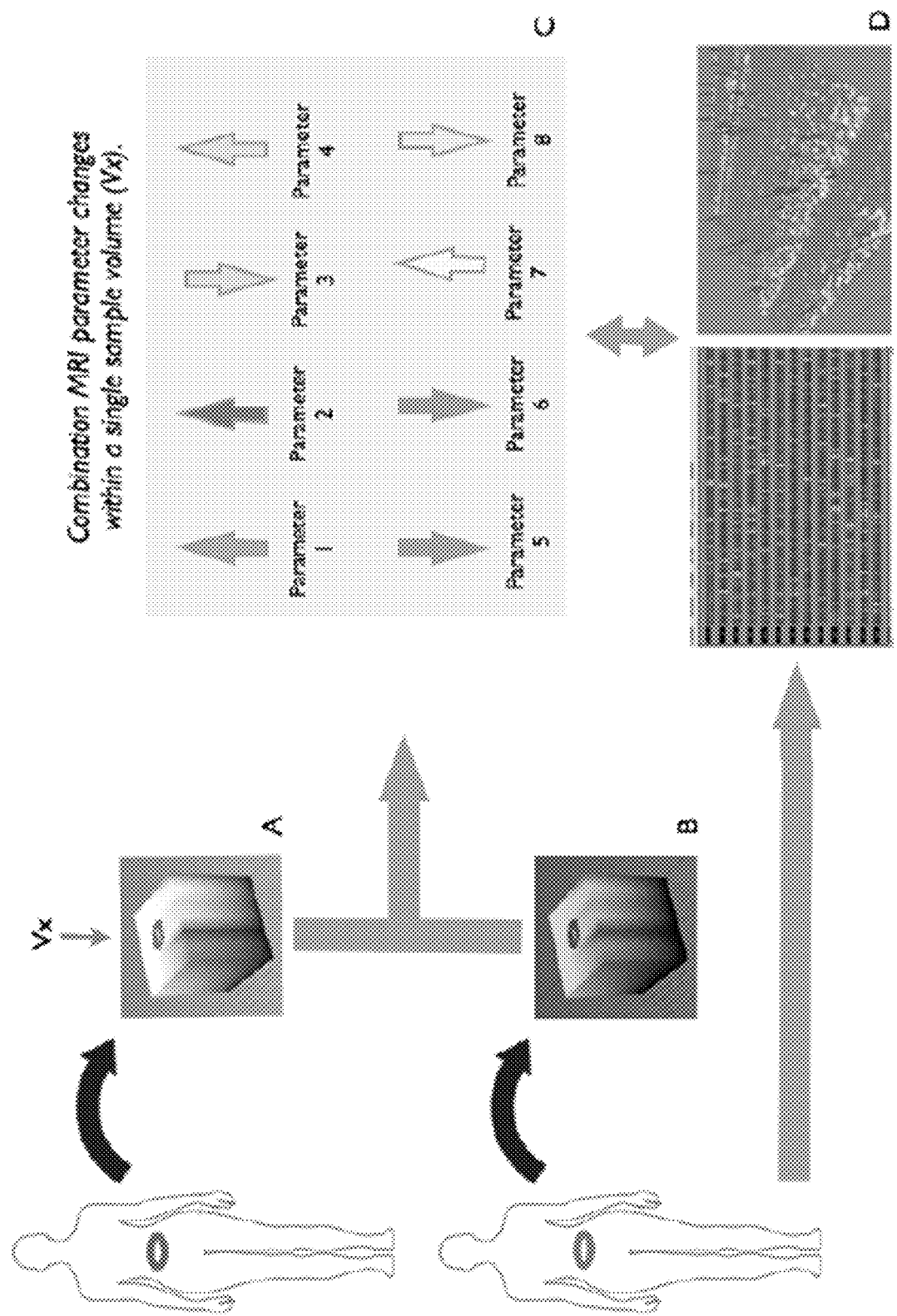
FIG. 3 is a schematic diagram of biomarker signatures of tumor response with multiparameter MRI.

A method for more precise characterization of tissue properties and changes from any in vivo tissue, including a wide array of post-treatment tissue changes, using array statistics and data mining techniques is provided in the present invention. Specifically, referring to FIGS. 2 and 3, this method can be used to identify biomarker signatures of tumor response or progression from densely sampled data matrix arrays of multiparameter MRI measures obtained from metastases in cancer patients. Referring to FIG. 2, densely overlapping grids of small ROI or kernels are used to create big-data 3D arrays of parameter measures. Multiple densely packed grids of small ROI (Vx) overlay a Ktrans map (A) of a lumbar vertebral body in a metastatic focus in a breast cancer patient. Dense sampling is used to generate a two-dimensional (2D) matrix for each MRI parameter (B). 2D matrices for each parameter may form a multi-parameter 3D data array (C). FIG. 3 illustrates a schematic diagram of the concept for obtaining biomarker signatures of tumor changes (response or progression) from 3D multiparameter MRI array datasets. Pre-drug (A) and post-drug (B) 3D arrays may be subtracted to obtain combinations of parameter changes (C). MRI combinations may be searched to determine "signatures" of tumor response or progression when analyzed in comparison to patient outcomes. If available, this MRI data may be compared to patient tumor tissue microarray data (D).

Figure 4:
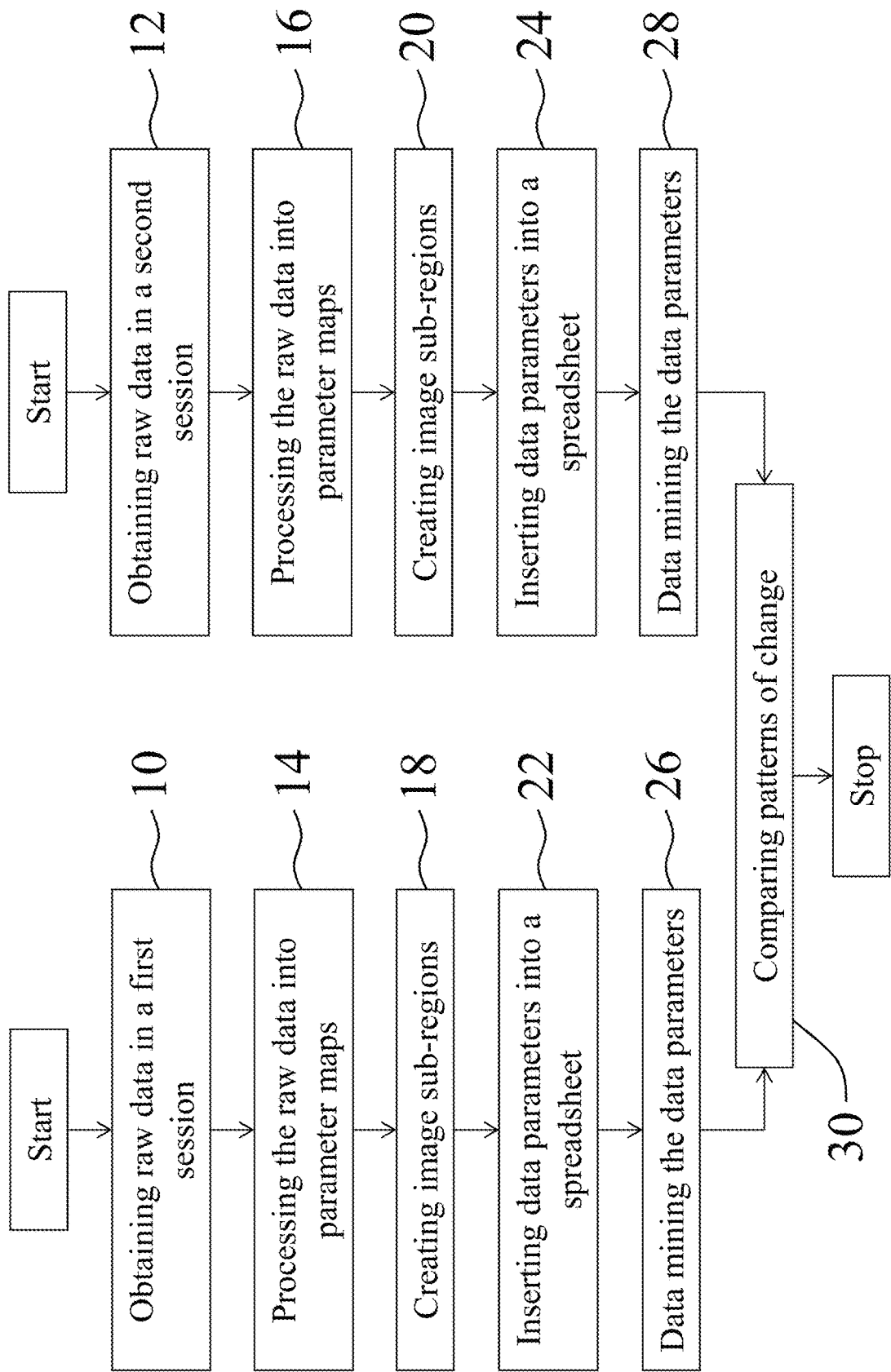
FIG. 4 is a flow chart of a tissue sampling method in accordance with the present invention.

With reference to FIG. 4, there is shown a flow chart of a tissue sampling method. The tissue sampling method may include: (1) obtaining raw data concerning in vivo tissue 100 in a first session or at a first time point (such as before treatment) and in a second or subsequent session or at a second time point (such as after treatment), as depicted in steps 10 and 12 of FIG. 4, wherein the raw data (such as MRI raw data) may be obtained from a MRI device or machine; (2) processing the raw data obtained in the steps 10 and 12 with a software package to obtain different parameter maps, as depicted in steps 14 and 16 of FIG. 4; (3) applying a grid over a region of interest using the software package to create multiple sub-regions of interest (SROIs), as depicted in steps 18 and 20 of FIG. 4; (4) inserting measures of different parameters concerning the sub-regions of interest (SROIs) within the in vivo tissue 100 into a spreadsheet program (or a matrix data collection software), as depicted in steps 22 and 24 of FIG. 4; and (5) data mining the measures of the different parameters to find patterns of tissue characteristics and/or changes (which may include identification of established tissue biomarkers), as depicted in steps 26 and 28 of FIG. 4. Optionally, as depicted in a step 30 of FIG. 4, comparison of the patterns of tissue characteristics and/or changes to true patient outcomes and biopsy results may be performed to determine tissue biomarkers applicable to individual patient care.

Figure 5:
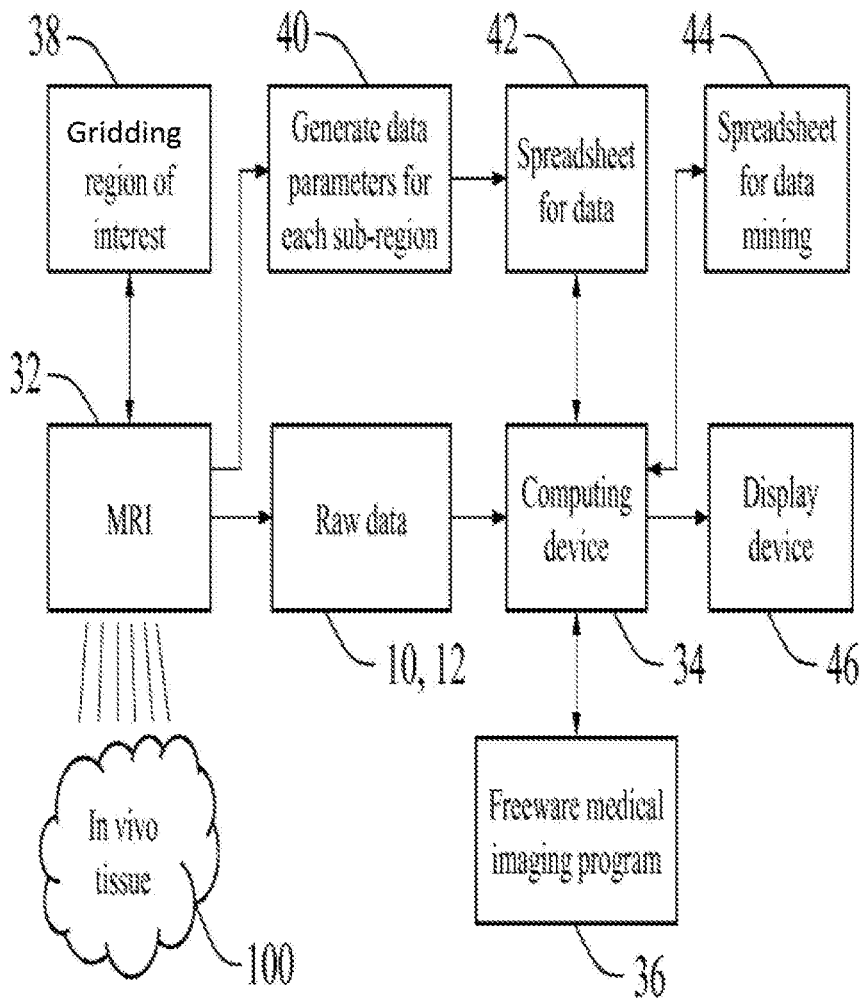
FIG. 5 is a schematic diagram of devices used to perform steps of a tissue sampling method in accordance with the present invention.

With reference to FIG. 5, a magnetic resonance imaging (MRI) device or machine 32 is used to obtain the raw data concerning the in vivo tissue 100. A software program 36, such as a freeware medical imaging software program or other commercially available software program, operates on a computing device 34 to obtain the different parameter maps from the raw data (e.g., MRI raw data) obtained in the steps 10 and 12. The computing device 34 may be any suitable computing device 34. The MRI device or machine 32 is also used to place a plurality of grids over a sub-region of interest (SROI) in box 38. The plurality of grids may create a plurality of sub-regions which may include but are not limited to the different parameters shown in box 40. The measures of the different parameters for each sub-region are entered into a spreadsheet 42, such as Excel or other matrix dataset collection software. The spreadsheet entries are data mined by a data mining software program 44, such as Excel Professional Plus or any other suitable software program, to find the patterns of tissue characteristics and/or changes in the SROI. The spreadsheet 42 may also be any other suitable software program or hardware. The data mining software program 44 may be any suitable software program or hardware. The patterns of tissue characteristics and/or changes are displayed on a display device 46, such as a computer monitor, to allow comparison to true patient outcomes and biopsy results to determine various tissue biomarkers.

It is preferable to identify SROI biomarkers of tissue characteristics and changes in a large number of patients to provide a baseline for SROI biomarkers in individual testing. Large scale clinical trials are needed in order to prove the validity of each biomarker for subsequent individual patient management, such as selecting individual cancer patient treatments. The multiple patients may be tested during treatment of various diseases (but specifically cancer) to determine various characteristics of the patient tissue. Specific examples may include but not be limited to 1) precise and sensitive identification of diseased tissue, 2) precise determination of tumor aggressiveness, 3) tumor tissue genetic characteristics, 4) tumor tissue or other tissue early response to therapy, and 5) tumor tissue or other tissue early signs of failure to therapy. This method may be applied across the entire patient body, from head-to-toe. Specifically, tissue may be sampled across the various metastatic clones in a single patient with metastatic cancer from whole-body MRI.

The method in the invention, for example, proposes using a potentially limitless combination of parameters. Examples may include but not be limited to multiple parameters from diffusion weighted imaging (DWI), multiple parameters from dynamic contrast-enhanced MRI (DCE-MRI), and could also potentially be used with a number of other parameters derived from various other MRI sequences. (FIG. 6).

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

What is claimed is:

1. A method for determining multiple parameters in a tissue, comprising:
receiving, by a computing device, multiple first parameter maps of an in vivo tissue based on raw data from a magnetic resonance imaging (MM) machine at a first time;
applying a first plurality of overlapping grids over a region of interest of each of the multiple first parameter maps, by the computing device, to create multiple sub-regions of interest, wherein each of the multiple first parameter maps corresponds to a parameter of the region of interest in the tissue;
obtaining, by the computing device, multiple first data parameter values for each of the sub-regions of interest from all of the multiple first parameter maps;
generating, by the computing device, a first plurality of two-dimensional matrices based on the multiple first data parameter values, wherein each respective two-dimensional matrix corresponds to an MRI parameter;
combining, by the computing device, the plurality of two-dimensional matrices to create a first three-dimensional multiparameter MRI array;
receiving, by the computing device, multiple second parameter maps at a second time after an event;
applying a second plurality of overlapping grids over a region of interest of each of the multiple second parameter maps, by the computing device, to create multiple sub-regions of interest, wherein each of the multiple second parameter maps corresponds to a parameter of the region of interest of each of the multiple second parameter maps;
obtaining, by the computing device, multiple second data parameter values for each of the sub-regions of interest from the multiple second parameter maps;
generating, by the computing device, a second plurality of two-dimensional matrices based on the multiple second data parameter values, wherein each respective two-dimensional matrix corresponds to an MRI parameter;
combining, by the computing device, the second plurality of two-dimensional matrices to create a second three-dimensional multiparameter MRI array;
subtracting, by the computing device, the first three-dimensional multiparameter MRI array from the second three-dimensional multiparameter MRI array to obtain one or more combinations of parameter changes; and
determining patterns of characteristics and change from the one or more combinations of parameter changes, wherein the patterns of characteristics and change comprise multiple identified tissue biomarkers for determining a diagnosis.

2. The method for determining multiple parameters in a tissue of claim 1, further comprising determining the identified tissue biomarkers through comparison of the patterns of characteristics and change to previously conducted clinical trials.

3. The method for determining multiple parameters in a tissue of claim 2, further comprising comparing the identified tissue biomarkers to biomarkers found during the large scale clinical trials.

4. The method for determining multiple parameters in a tissue of claim 1, further comprising using multiple changes of the identified tissue biomarkers in said sub-regions of interest for clinical management.

5. The method for determining multiple parameters in a tissue of claim 1, further comprising displaying the patterns of characteristics and change on a computer monitor.

6. The method for determining multiple parameters in a tissue of claim 1, further comprising mining, via the computing device, multiple second data parameter measures for each of the sub-regions of interest.

7. The method for determining multiple parameters in a tissue of claim 1, further comprising registering the multiple parameter maps such that each of the multiple sub-regions of interest correspond to a respective sub-region of interest of the other multiple parameter maps.

8. The method for determining multiple parameters in a tissue of claim 1, wherein the event is a surgery.

9. The method for determining multiple parameters in a tissue of claim 1, wherein the event comprises application of a medication to the tissue.

10. The method for determining multiple parameters in a tissue of claim 1, wherein the patterns of characteristics and change from the one or more combinations of parameter changes indicate a trajectory in the tissue.

11. The method for determining multiple parameters in a tissue of claim 1, wherein the patterns of characteristics and change comprise multiple identified tissue biomarkers.

12. The method for determining multiple parameters in a tissue of claim 1, wherein one of the multiple parameter maps comprise Ktrans and Ve parameters.

13. The method for determining multiple parameters in a tissue of claim 1, wherein one of the multiple parameter maps comprise T1 and T2 parameters.

14. The method for determining multiple parameters in a tissue of claim 1, further comprising determining at least one tissue biomarker using the first data parameter values.

\* \* \* \* \*